Figure 1:
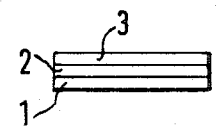

United States Patent [19]

Ball

[11] 4,451,816
[45] May 29, 1984

[54] GAS MONITOR

[76] Inventor: Geoffrey W. Ball, Apple Patch, Bellingdon, Chesham, Buckinghamshire, England

[21] Appl. No.: 336,403

[22] Filed: Dec. 31, 1981

[30] Foreign Application Priority Data

Dec. 31, 1980 [GB] United Kingdom ................ 8041552

[51] Int. Cl.³ .............................................. H01L 7/00
[52] U.S. Cl. .................................... 338/34; 73/27 R; 422/98
[58] Field of Search ........................... 338/34, 35, 308; 340/632-634; 200/61.03; 422/87, 88, 94, 98; 73/27 R

[56] References Cited

U.S. PATENT DOCUMENTS

| | | | |
|---|---|---|---|
| 3,603,954 | 9/1971 | Takeuchi | 422/98 X |
| 3,631,436 | 12/1971 | Taguchi | 422/98 X |
| 3,714,562 | 1/1973 | McNerney | 73/27 X |
| 3,924,219 | 12/1975 | Braun | 338/34 |
| 3,950,980 | 4/1976 | Braun et al. | 338/34 |
| 4,235,097 | 11/1980 | Kring et al. | 422/88 X |

Primary Examiner—C. L. Albritton
Attorney, Agent, or Firm—Cushman, Darby & Cushman

[57] ABSTRACT

A gas monitor comprises a tape having a layer of gas absorbant material carried by a base. The base and the layer of gas absorbant material are capable of being heated, without being damaged, to a temperature at which any gas absorbed by the gas absorbant material is driven off.

9 Claims, 3 Drawing Figures

GAS MONITOR

This invention relates to a gas monitor.

It is now legal in many places that any work area in a factory in which toxic gases are to be found is subject to monitoring. For this purpose, it is known to provide a passive monitor which normally consists of a layer of an absorbant material carried by a membrane and supported by some housing. A passive monitor is normally quite small and can be attached to the clothing of an employee working in the area in which the toxic gases may occur. An employee wears a particular monitor during the whole of one work period. After that work period, the absorbant material is removed from the monitor and is subjected to analysis, normally by a mass spectrometer or any other analyser. This does give a value, for each gas, of the integrated value of that gas present in the vicinity of that employee during the work period, and to that extent gives an indication of the quantity of noxious gas to which that employee was subjected. It is of course normally the case that at any given work atmosphere, there is only present one noxious gas which must be monitored but sometimes two or more noxious gases must be monitored. However, this passive monitor would not give any indication of a very high concentration of noxious gas for a short period and such a high concentration of noxious gas for a short period might in fact be very dangerous.

It is also known to provide a paper tape type monitor in which paper impregnated with a chemical which changes colour in the presence of a noxious gas, which is to be monitored, is driven from one reel onto another reel and in its passage between the two reels becomes exposed to the atmosphere which is to be monitored. Such a paper tape monitor, which is an example of an active gas monitor, may be sufficiently small to be carried on the clothing of an employee or may be part of a relatively large piece of equipment disposed in the work area in which the employee is located. The paper tape is adjusted to colormetric analysis either in real time or after the end of the work period; the optical equipment used for colormetric analysis includes a light source and a light detector.

This type of paper tape detector has the disadvantage that while it gives an indication of a sudden concentration of noxious gas, it does not give the average value of the noxious gas during the entire work period and it should be appreciated that both values are important. A paper tape monitor also has the disadvantage that the chemical with which the paper is impregnated is normally only responsive to one particular noxious gas. If it does respond to more than one noxious gas interference will occur in that each gas will cause the same colour change and it is impossible to ascertain for the paper tape which noxious gas is present.

It is an object of this invention to provide a gas monitor which alleviates at least one of the disadvantages set out above of the known gas monitors.

According to this invention, there is provided a gas monitor comprising a tape having a base carrying a layer of gas absorbant material capable of recording magnetic signals, both the base and the layer of gas absorbant material being capable of being heated to a temperature at which any gas absorbed by the gas absorbant material is driven off without being damaged.

It is possible to record any desired signal on the gas absorbant layer which is capable of recording magnetic signals, although that layer has the primary function of absorbing gases. The information recorded can be the name of the wearer of the monitor, a time signal or any other information desired.

According to another aspect of this invention, there is provided an analyser for a gas monitor as set out in the preceding paragraph, the analyzer comprising a heater and a gas detector having its gas inlet facing the heater so that the monitor may be disposed between the heater and the inlet and the heater activated whereupon the absorbed gases are driven off and enter the inlet directly.

The gas detector is desirably a mass spectrometer.

In a preferred embodiment, the gas monitor further comprises a housing in which the tape is disposed, the housing having an aperture, and means for driving the tape so that it passes in front of the aperture in which position only the layer of gas absorbant material is exposed to the ambient atmosphere.

Preferably, the base of the tape is metal so that no gases are given off by the base when it is heated; however, the base could be of plastics material.

It has been found that ferric oxide is a suitable material for the said layer and that some tapes currently sold for conventional audio tape recorders consisting of a metal base carrying a layer of ferric oxide are suitable for incorporation into the preferred embodiment of this invention.

The analyser may have a construction generally similar to that of the conventional tape recorder and in which the tape is driven between the heater and the inlet to the gas detector.

In another form of the invention in which the gas monitor is of the passive type, the base and layer are held within a housing and the layer is covered by a membrane.

With the passive monitor in accordance with this invention, the gas monitors, after use, are desirably presented sequentially between the heater and the detector of the gas analyser, the mechanism for effecting the sequential presentation being identical to that used in the domestic slide projector.

A gas monitor in the form of the preferred embodiment has the advantages that it is possible to electrically integrate the output signal from the detector. Secondly, the detector will indicate the value of all gas components which have been absorbed by the layer. Thirdly, there is unlikely to be interference between one noxious gas and another noxious gas and fourthly, the response is relatively rapid.

Figure 2:
Figure 3:
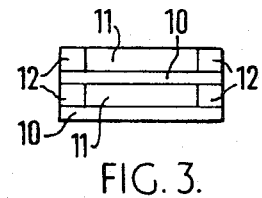

Embodiments of this invention will now be described, by way of example, with reference to the accompanying drawings of which FIGS. 1 to 3 are each a cross-sectional view of a tape forming part of a gas monitor in accordance with this invention. Corresponding integers in FIGS. 1 and 2 have the same reference numerals.

The cross-section of a tape forming part of a gas monitor in accordance with this invention may be as illustrated in FIG. 1 which has a metal base 1 on which is formed a layer 2 of a gas absorbant material covered by a membrane 3. In this embodiment the material of the layer 2 may be ferric oxide.

In the embodiment of FIG. 2, the membrane 3 is covered by another layer 4 of gas absorbant material in turn covered by a second membrane 5. The layers 2 and 3 are of different materials and the layer 4 is also permeable to certain gases. The membrane 5 has a tendency to select only certain gases present in the atmosphere and these are passed through to the layer 4 which absorbs some of those gases and passes some through to the membrane 3. The membrane 3 only passes certain of the gases through to the layer 2 which absorbs those gases.

Referring now to FIG. 3, there is shown two layers of a tape of a gas monitor in accordance with this invention one wound on top of the other. Each layer of tape comprises a metal base 10, a layer 11 of gas absorbant material, the layer 11 being narrower than the base 10 and being confined by impermeable strips 12 extending along the edge of the base 10. With this arrangement when one layer of tape is wound on top of another layer, the layer 11 of gas absorbant material of that type is wholly enclosed and cannot absorb any material. This has the result that the gas absorbant layer 11 is only exposed to the ambient atmosphere when it is not on one of the reels forming part of the gas monitor.

What is claimed is:

1. A gas monitor comprising:
   a tape having a base carrying a layer of gas absorbant material capable of recording magnetic signals,
   both the base and the layer of gas absorbant material being capable of being heated to a temperature at which any gas absorbed by the gas absorbant material is driven off without being damaged.

2. A gas monitor as claimed in claim 1 which comprises a gas permeable membrane which covers the layer and is capable of being heated to the said temperature without being damaged.

3. A gas monitor as claimed in claim 2 which comprises a further layer of gas absorbant material carried by the said membrane and a further gas permeable membrane which covers the further layer, the base, both layers and both membranes being capable of being heated to a temperature at which any gas absorbed by either layer of gas permeable material is driven off without being damaged.

4. A gas monitor as claimed in claim 1 wherein the layer of gas absorbant material covers a central portion of the base and which comprises strips of impermeable material which cover the base on each side of the layer of gas absorbant material.

5. A gas monitor as claimed in claim 1 wherein the base is of metal.

6. A gas monitor as claimed in claim 1 wherein the gas monitor material is ferric oxide.

7. A gas monitor as claimed in claim 1 comprising a housing in which the tape is disposed, the housing having an aperture, and means for driving the tape so that it passes in front of the aperture in which position only the layer of gas absorbant material is exposed to the ambient atmosphere.

8. A gas monitor as claimed in claim 1 which comprises a housing in which the base and layer of gas absorbant material are held, and a membrane which covers the layer of gas absorbant material.

9. An analyser for a gas monitor as claimed in claim 1, the analyzer comprising a heater and a gas detector, the gas detector having a gas inlet facing the heater so that the monitor may be disposed between the heater and the inlet and the heater activated whereupon the gases absorbed by the layer of gas absorbant material of the monitor are driven off and enter the gas inlet directly.

* * * * *